United States Patent
Witowski et al.

(10) Patent No.: US 10,709,748 B2
(45) Date of Patent: Jul. 14, 2020

(54) ENCAPSULATED CANNABINOID FORMULATIONS FOR TRANSDERMAL DELIVERY

(71) Applicant: Nutrae, LLC, Sarasota, FL (US)

(72) Inventors: Christopher G. Witowski, Tampa, FL (US); Jacqueline L. Salm, Tampa, FL (US)

(73) Assignee: NUTRAE, LLC, Sarasota, FL (US)

( * ) Notice: Subject to any disclaimer, the term of this patent is extended or adjusted under 35 U.S.C. 154(b) by 0 days.

(21) Appl. No.: 16/246,411

(22) Filed: Jan. 11, 2019

(65) Prior Publication Data

US 2019/0216870 A1 Jul. 18, 2019

Related U.S. Application Data

(60) Provisional application No. 62/617,003, filed on Jan. 12, 2018.

(51) Int. Cl.
| | |
|---|---|
| *A61K 36/00* | (2006.01) |
| *A61K 36/185* | (2006.01) |
| *A61K 9/00* | (2006.01) |
| *A61K 45/06* | (2006.01) |
| *A61K 31/352* | (2006.01) |
| *A23L 33/105* | (2016.01) |
| *A23L 2/56* | (2006.01) |
| *A61K 9/107* | (2006.01) |
| *A61K 47/10* | (2017.01) |
| *A61K 9/70* | (2006.01) |
| *A61K 31/05* | (2006.01) |
| *A61K 31/192* | (2006.01) |

(52) U.S. Cl.
CPC .............. *A61K 36/185* (2013.01); *A23L 2/56* (2013.01); *A23L 33/105* (2016.08); *A61K 9/006* (2013.01); *A61K 9/0014* (2013.01); *A61K 9/0019* (2013.01); *A61K 9/0073* (2013.01); *A61K 9/1075* (2013.01); *A61K 9/7084* (2013.01); *A61K 31/352* (2013.01); *A61K 45/06* (2013.01); *A61K 47/10* (2013.01); *A23V 2002/00* (2013.01); *A23V 2200/242* (2013.01); *A23V 2250/2132* (2013.01); *A61K 31/05* (2013.01); *A61K 31/192* (2013.01)

(58) Field of Classification Search
None
See application file for complete search history.

(56) References Cited

U.S. PATENT DOCUMENTS

| | | | |
|---|---|---|---|
| 2005/0266061 | A1 | 12/2005 | Stinchcomb et al. |
| 2014/0357708 | A1 | 12/2014 | Murty et al. |
| 2015/0126595 | A1 | 5/2015 | Smith |
| 2016/0303039 | A1 | 10/2016 | Smith et al. |
| 2019/0110981 | A1* | 4/2019 | Weimann ................ A61K 9/006 |
| 2019/0133994 | A1* | 5/2019 | Smith .................. A61K 31/352 |

FOREIGN PATENT DOCUMENTS

| | | |
|---|---|---|
| AU | 2013213706 B2 | 8/2013 |
| WO | 200103668 A1 | 1/2001 |
| WO | 2002064109 A2 | 8/2002 |
| WO | 2012033478 A1 | 3/2012 |
| WO | 2015161165 A1 | 10/2015 |
| WO | 2015200049 A1 | 12/2015 |
| WO | 2016147186 A1 | 9/2016 |

OTHER PUBLICATIONS

Officer Jose Ruiz Fernandez; International Search Report and Written Opinion; PCT/US2019/013376; dated Mar. 29, 2019; 12 pages.
Officer Jose Ruiz Fernandez; International Search Report and Written Opinion; PCT/US2019/013374; dated Mar. 29, 2019; 23 pages.
Officer Anita Meacle; International Search Report and Written Opinion; PCT/US2019/013374; dated Apr. 5, 2019; 12 pages.

* cited by examiner

*Primary Examiner* — Michael Barker
*Assistant Examiner* — Randall Winston
(74) *Attorney, Agent, or Firm* — Dickinson Wright PLLC; Kristopher Lance Anderson (57) ABSTRACT

Preparation of cannabinoid formulations containing: Δ9-tetrahydrocannabinol (Δ9-THC), Δ8-tetrahydrocannabinol (Δ8-THC), Δ9-tetrahydrocannabinolic acid (THCa), cannabidiol (CBD), cannabidiolic acid (CBDa), cannabigerol (CBG), cannabichromene (CBC) and cannabinol (CBN), either alone or in combinations henceforth known as *cannabis*, have been created using an emulsification process to encapsulate cannabinoids. The aqueous-based method involves micellular encapsulation of cannabinoids, a method that has been used to increase the bioavailability of poorly permeable, lipophilic drugs. The present invention demonstrates the viability of transdermal delivery with gels and patches for consistent and sustained cannabinoid dosing.

14 Claims, 6 Drawing Sheets

ENCAPSULATED CANNABINOID FORMULATIONS FOR TRANSDERMAL DELIVERY

CROSS-REFERENCE TO RELATED APPLICATIONS

This application claims priority to U.S. Provisional Patent Application Ser. No. 62/617,003, filed on Jan. 12, 2018, entitled "ENCAPSULATED CANNABINOID FORMULATIONS" of which is hereby incorporated herein by reference in their entirety for all purposes.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present disclosure relates in general to the field of drug delivery formulations. In particular, the present disclosure provides for the encapsulation of poorly soluble cannabinoids for efficient transdermal delivery to a subject.

BACKGROUND

*Cannabis* is an annual, primarily dioecious, flowering herb. The genera *Cannabis* is considered to be monospecific (*Cannabis sativa* L.) which is divided into several subspecies (*C. sativa* subsp.*sativa, C. sativa* subsp. *indica, C. sativa* subsp. *ruderalis, C. sativa* subsp. *spontanea, C. sativa* subsp. *kafiristanca*). However, the chemical and morphological distinctions by which *cannabis* has been split into these subspecies are often not readily discernible, appear to be environmentally modifiable, and vary in a continuous fashion. For most purposes, it will suffice to apply the name *Cannabis sativa* to all *cannabis* plants encountered.

Cannabinoids are chemical compounds found in the *cannabis* plant that interact with receptors in the brain and body to create various effects. *Cannabis* contains over 400 compounds including over 100 cannabinoids, which are aryl-substituted meroterpenes unique to the plant genus *cannabis*. The pharmacology of most of the cannabinoids is largely unknown but the most potent psychoactive agent, $\Delta^9$-tetrahydrocannabinol ($\Delta^9$-THC, or THC), has been isolated, synthesized and much studied due to its abundance and psychoactive attributes. Other plant-based cannabinoids include $\Delta^9$-tetrahydrocannabinolic acid, $\Delta^8$-THC, cannabigerol, cannabidiolic acid, and cannabidiol (CBD). These and other cannabinoids have additive, synergistic or antagonistic effects with THC and may modify its actions when *cannabis* products are consumed.

Cannabinoid containing extracts can be produced from a wide variety of methods (sub/supercritical $CO_2$, hydrocarbons, alcohols, and by heated/pressurized means) and can be further purified using winterization (precipitation) in alcohols, distillation, or chromatographic separation. The resulting cannabinoids are highly lipophilic with Log P values ranging from 5 to 9, making them practically insoluble in water. These properties are not conducive to traditional pharmaceutical drug delivery methods, which is why smoking is still a preferred method for *cannabis* consumption.

It is well known in cosmeceutical and pharmaceutical preparations that above the critical micelle concentration of one or more surfactants that micelles will be formed during emulsification. The micelles can take many shapes (spherical, cylinders, or other arrangements), structures (unilamellar or multilamellar), and names (liposomes, niosomes, and ethosomes among others). Various reports have concluded that these micelles can also be used to encapsulate active ingredients for delivery of pharmaceuticals (Hung et al. 2001; Narang et al. 2007; Kwon, 2012) as well as increase the bioavailability of drugs with poor water solubility (Keller et al. 1999; Touitou et al. 2000; O'Driscoll et al. 2008).

Transdermal delivery allows for direct absorption into the bloodstream without a hepatic first pass effect that significantly reduces the bioavailability of cannabinoids. Despite efforts to create highly soluble and bioavailable cannabinoid formulations, there remains a need in the art for cannabinoid formulations that have increased bioavailability and which are conducive to use with traditional drug delivery methods.

SUMMARY OF THE DISCLOSURE

It is therefore an object of the present disclosure to provide water-soluble cannabinoid formulations that are surfactant-stabilized and that have increased bioavailability.

In one aspect of the present disclosure, various preparations are presented to produce an oil-in-water emulsion in which the hydrophilic-lipophilic balance (HLB) is optimized to produce a stable emulsion. A blend of surfactants can increase the stability of emulsions and create self-emulsifying drug delivery systems (SEDDS). During emulsification, micelles are created which have the ability to capture cannabinoids and other *cannabis*-based ingredients within the hydrophobic inner core. The encapsulation protects labile ingredients and the hydrophilic heads of the micellular outer shell increase drug delivery capabilities.

In one aspect of the present disclosure, a cannabinoid composition is provided, said composition comprising: a cannabinoid preparation; at least one surfactant; at least one co-solvent; and water; wherein said cannabinoid composition yields the cannabinoid preparation capable of having increased bioavailability. In another aspect, the at least one surfactant comprises one or more, or alternatively, at least two surfactants. Further, the one or more surfactants have an HLB in the range of 1 to 8 and form a self-assembling emulsion. In another aspect, at least one surfactant comprises an HLB in the range of 9-20. In yet another aspect, the at least one surfactant is selected from a group consisting of: oleic acid, sunflower oil, lecithin, phosphatidylcholine, isopropyl myristate, stearic acid, medium and long chain triglycerides, Labrasol, polysorbate 20, polysorbate 80, or other ethoxylated surfactant, and sorbitan trioleate, or other sorbitan surfactant.

In another aspect of the present disclosure, the at least one co-solvent is selected from a group consisting of: methanol, ethanol, isopropyl alcohol, butanol, pentanol, hexanol, ethylene glycol, propylene glycol, dipropylene glycol, glycerol, erythritol, xylitol, mannitol, sorbitol, diethylene glycol monoethyl ether (Transcutol), any derivative thereof, and combinations relating thereto.

In one aspect cannabinoid preparation of the present disclosure is encapsulated by surfactants to form micelles having uni-, bi-, or multi-lamellar structures.

In another aspect, the composition of the present disclosure comprises a stabilizer in the range of 0.01% to 3% (w/w). In yet another aspect, the composition comprises a thickening agent in the range of 0.01% to 5% (w/w). In another aspect, the composition comprises terpenes in the range of 0.1% to 5% (w/w). In another aspect, the total cannabinoid preparation of the present disclosure ranges from 0.01% to 20% (w/w), the at least one surfactants range from 5% to 50% (w/w), the at least one co-solvents range from 10% to 70% (w/w), the water ranges from 16% to 60% (w/w), and the stabilizer ranges from 0.01% to 3% (w/w).

It is a further object of the present disclosure to provide a composition capable of transdermal delivery. In one aspect, a cannabinoid composition is provided that is capable of transdermal delivery, comprising: a cannabinoid composition further comprising: a cannabinoid preparation ranging from 0.1% to 10% (w/w); at least one surfactant ranging from 0.1% to 25% (w/w); at least one co-solvent ranging from 10% to 60% (w/w); water ranging from 16% to 60% (w/w); a stabilizer ranging from 0.01% to 3% (w/w); and a patch comprised of a reservoir and a backing film sealed to a membrane having an adhesive; wherein the patch reservoir is capable of operably containing the cannabinoid composition within the backing film, and is capable of operably affixing to skin via the adhesive for transdermal delivery of the cannabinoid composition.

It is a further object of the present disclosure to provide a cannabinoid composition, said composition comprising a cannabinoid preparation, at least one surfactant, at least one co-solvent; and water; wherein said cannabinoid composition yields the cannabinoid preparation capable of having increased bioavailability. In one aspect the at least one surfactant comprises one or more surfactants. In another aspect, the two surfactants comprise an HLB in the range of 1 to 8 and form a self-assembling emulsion. In even another aspect, the at least one surfactant comprises an HLB in the range of 9-20. The at least one surfactant may therefore be selected from a group consisting of: oleic acid, sunflower oil, lecithin, phosphatidylcholine, isopropyl myristate, stearic acid, medium and long chain triglycerides, Labrasol, polysorbate 20, polysorbate 80, or other ethoxylated surfactant, and sorbitan trioleate, or other sorbitan surfactant.

In one aspect the at least one co-solvent is selected from a group consisting of: methanol, ethanol, isopropyl alcohol, butanol, pentanol, hexanol, ethylene glycol, propylene glycol, dipropylene glycol, glycerol, erythritol, xylitol, mannitol, sorbitol, diethylene glycol monoethyl ether (Transcutol), any derivative thereof, and combinations relating thereto.

In another aspect of the present disclosure, the cannabinoid preparation is encapsulated by surfactants to form micelles having uni-, bi-, or multi-lamellar structures. The cannabinoid composition may further comprise a stabilizer in the range of 0.01% to 3% (w/w). The cannabinoid composition may further comprise a thickening agent in the range of 0.01% to 5% (w/w). The cannabinoid composition may even further comprise terpenes in the range of 0.1% to 5% (w/w). In another aspect the cannabinoid preparation ranges from 0.1% to 20% (w/w), the at least one surfactants range from 5% to 50% (w/w), the at least one co-solvents range from 5% to 70% (w/w), the water ranges from 16% to 60% (w/w), and the stabilizer ranges from 0.01% to 3% (w/w).

It is another object of the present disclosure to provide a composition that is capable of transdermal delivery. In one aspect, the composition comprises: a cannabinoid composition further comprising a cannabinoid preparation ranging from 0.1% to 10% (w/w), at least one surfactant ranging from 0.1% to 25% (w/w), at least one co-solvent ranging from 10% to 70% (w/w), water ranging from 16% to 60% (w/w), a stabilizer ranging from 0.01% to 3% (w/w); and a patch comprised of a reservoir and a backing film sealed to a membrane having an adhesive; wherein the patch reservoir is capable of operably containing the cannabinoid composition within the backing film, and is capable of operably affixing to skin via the adhesive for transdermal delivery of the cannabinoid composition.

In another aspect, the cannabinoid composition composes a cannabinoid preparation ranging from 0.1% to 3% (w/w), at least one surfactant ranging from 0.1% to 15% (w/w), at least one co-solvent ranging from 10% to 50% (w/w), water ranging from 50% to 99% (w/w), a stabilizer ranging from 0.01 to 3% (w/w); wherein said composition yields the cannabinoid preparation capable of having increased bioavailability. In one aspect the composition further comprises a preservative ranging from 0.01% to 2.5% (w/w).

In another aspect, the present disclosure provides a method for preparing a cannabinoid composition having increased bioavailability, the method comprising forming a cannabinoid composition comprising: preparing an oil phase composition comprising, a cannabinoid preparation, at least one surfactant; and at least one co-solvent, preparing a water phase composition comprising water and a stabilizing agent, mixing the oil phase composition and the water phase composition under high shear conditions to form micelles within a microemulsion, sonicating the microemulsion to increase the micelles and decrease the particle size of said micelles, centrifugation to purify micelles and/or further create micelles and introducing a second water phase composition comprising water and a stabilizing agent, wherein said cannabinoid composition yields the cannabinoid preparation capable of having increased bioavailability.

It is another object of the present invention to provide a cannabinoid composition capable of transdermal delivery, comprising: a cannabinoid composition further comprising: a cannabinoid preparation ranging from 0.1% to 20% (w/w); at least one surfactant ranging from 5% to 50% (w/w); at least one co-solvent ranging from 10% to 70% (w/w); water ranging from 16% to 60% (w/w); and wherein the cannabinoid composition is capable of topical application.

In one aspect the at least one surfactant comprises two surfactants. In another aspect the two surfactants comprise an HLB in the range of 1 to 8 and form a self-assembling emulsion. In another aspect the at least one surfactant comprises an HLB in the range of 9-20. In yet another aspect the at least one surfactant is selected from a group consisting of: oleic acid, lecithin, phosphatidylcholine, isopropyl myristate, stearic acid, medium and long chain triglycerides (including Labrasol), polysorbate 20, polysorbate 80, or other ethoxylated surfactant, and sorbitan trioleate, or other sorbitan surfactant.

In another aspect the at least one co-solvent is selected from a group consisting of; methanol, ethanol, isopropyl alcohol, butanol, pentanol, hexanol, ethylene glycol, propylene glycol, dipropylene glycol, glycerol, erythritol, xylitol, mannitol, sorbitol, diethylene glycol monoethyl ether (Transcutol), any derivative thereof, and combinations relating thereto.

The cannabinoid preparation within the cannabinoid composition is encapsulated by surfactants to form micelles having uni-, bi-, or multi-lamellar structures.

In another aspect the cannabinoid composition further comprises a stabilizer in the range of 0.01% to 3% (w/w). In another aspect the cannabinoid composition further comprises a thickening agent in the range of 0.01% to 5% (w/w). In another aspect the cannabinoid composition further comprises terpenes in the range of 0.1% to 5% (w/w).

In another aspect, the cannabinoid preparation ranges from 0.1% to 3% (w/w), the at least one surfactants range from 0.1% to 15% (w/w), the at least one co-solvents range from 0.1% to 50% (w/w), the water ranges from 50% to 99% (w/w), and the stabilizer ranges from 0.01% to 3% (w/w).

In another aspect the cannabinoid composition further comprises a preservative ranging from 0.01% to 2.5% (w/w). In another aspect the cannabinoid composition further comprises a pH modifying agent to neutralize the composition.

In another aspect, the cannabinoid composition is incorporated into a patch comprised of a reservoir and a backing film having an adhesive; wherein the patch reservoir is capable of operably containing the cannabinoid composition within the backing film, and is capable of operably affixing to skin via the adhesive for transdermal delivery of the cannabinoid composition. The patch may further comprise a rate-controlling membrane. In another aspect, the patch may further comprise a drug encased reservoir.

It is another object of the present invention to provide a cannabinoid composition for topical application in the form of an ointment, a cream, an emulsion, a lotion, a paste, an unguent, a gel or a sunscreen comprising therapeutically effective amounts of the cannabinoid composition.

In another aspect, the present invention provides a method for preparing a cannabinoid composition for transdermal delivery, the method comprising forming a cannabinoid composition comprising: preparing an oil phase composition comprising: a cannabinoid preparation; at least one surfactant; and at least one co-solvent; preparing a water phase composition comprising: water; mixing the oil phase composition and the water phase composition to form micelles within a microemulsion; centrifugation to purify micelles and/or further create micelles; and introducing a second water phase composition comprising: water; and a stabilizing agent; wherein said cannabinoid composition is capable of topical administration.

In another aspect the present invention provides a method for preparing a cannabinoid composition for transdermal delivery, the method comprising forming a cannabinoid composition comprising: preparing an oil phase composition comprising: a cannabinoid preparation; at least one surfactant; and at least one co-solvent; preparing a water phase composition comprising: water; and a stabilizing agent; mixing the oil phase composition and the water phase composition to form micelles within a microemulsion; wherein said cannabinoid composition is capable of transdermal delivery.

In another aspect the present invention provides a method for treating a subject, comprising: topically administering a cannabinoid composition into the subject in a dose amount effective to treat the subject's symptoms; wherein the transdermal cannabinoid composition comprises: an oil phase composition comprising: a cannabinoid preparation; at least one surfactant; and at least one co-solvent; a water phase composition comprising water; and a stabilizing agent; wherein the oil phase composition and the water phase composition are mixed to form micelles within a microemulsion; wherein said cannabinoid composition yields the cannabinoid preparation capable of having increased bioavailability when topically administered.

In one aspect, the disclosed methods further include sonicating the microemulsion to increase the micelles and decrease the particle size of said micelles. In one aspect, the at least one surfactant is at least one nonionic surfactant to encapsulate the cannabinoid preparation.

In another aspect the cannabinoid composition is applied topically. In one aspect the cannabinoid composition suitable for topical application in the form of an ointment, a cream, an emulsion, a lotion, a paste, an unguent, a gel or a sunscreen comprising therapeutically effective amounts of the cannabinoid composition. In another aspect the cannabinoid composition is incorporated into a patch comprising a patch reservoir backing film and an adhesive; wherein the patch reservoir is capable of operably containing the cannabinoid composition within the backing film, and is capable of operably affixing to skin via the adhesive for transdermal delivery of the cannabinoid composition. In yet another aspect the cannabinoid compositions is capable of delivering a sustained, therapeutic dose of the cannabinoid preparation for at least 72 hours.

In one aspect the patch reservoir is a drug encased reservoir. In another aspect, the methods described herein include a membrane sealed to the patch reservoir backing film. The membrane may further comprise a rate-controlling membrane.

In a further aspect, the present invention provides a method for delivering cannabinoids topically using nonionic surfactants to encapsulate and further increase bioavailability of cannabinoids for transdermal delivery. In yet another aspect, the present disclosure provides a method for encapsulating cannabinoids using nonionic surfactants and deliver a sustained, therapeutic dose over 72 hours. In a further aspect, the method implements a transdermal patch. The patch may further comprise a rate-controlling membrane. The patch may further comprise a drug encased reservoir.

BRIEF DESCRIPTION OF THE DRAWINGS

The present invention is further described in the detailed description which follows, in reference to the noted plurality of drawings by way of non-limiting examples of exemplary embodiments, in which like reference numerals represent similar parts throughout the several views of the drawings, and wherein.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

While the making and using of various embodiments of the present disclosure are discussed in detail below, it should be appreciated that the present disclosure provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the instant disclosure may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Also, it is noted that individual embodiments may be described as a process which is depicted as a flowchart, a flow diagram, or a block diagram. Although a flowchart may describe the operations as a sequential process, many of the operations can be performed in parallel or concurrently. In addition, the order of the operations may be re-arranged.

It has been shown that self-emulsifying drug delivery systems (SEDDS), which are isotropic mixtures of oils, surfactants, solvents and co-solvents/surfactants, can be used for the design of formulations in order to improve the absorption of highly lipophilic drug compounds. Although the exact mechanisms responsible for the enhanced absorption and bioavailability are not fully known, it is believed that various factors, including improved drug solubilization, act to increase the particle diffusion through membranes and/or the point of absorption. The advantages of these systems include not only improved drug solubilization but also enhanced release and absorption properties due to the already dissolved form of the drug in the formulation and the resulting small droplet size, which provides a large interfacial surface area.

The efficiency of absorption of the drug compound from the SEDDS is dependent on many formulation-related parameters, including oil/surfactant ratios, surfactant concentration, polarity or hydrophobic-lipophilic balance of the resulting emulsion, droplet size and charge, the combination of which determines the self-emulsification ability. All of these factors must be designed to accommodate the desired drug, typically a single compound or salt derivative. As a result, only very specific pharmaceutical excipient combinations actually lead to efficient self-emulsifying systems. Although many studies have been carried out, there are few transdermal drug products on the pharmaceutical market formulated as SEDDS, confirming the difficulty of formulating hydrophobic drug compounds into such delivery systems.

Of even greater difficulty are the use of extracted oils such as *cannabis* derived oils and related derivatives, including chemical substances related to tetrahydrocannabinol (THC) and its acid form THCa, cannabidiol (CBD) and its acid form CBDa, cannabinol (CBN), cannabigerol (CBG), tetrahydrocannabivarin (THCV), cannabichromene (CBC), and other substances that bind to cannabinoid receptors. Other known cannabinoids include tetrahydrocannabinol, $\Delta^8$-tetrahydrocannabinol, $\Delta^8$-tetrahydrocannabinol-DMH, $\Delta^9$-tetrahydrocannabinol propyl analogue (THCV), 11-hydroxy-tetrahydrocannabinol, 11-nor-9-carboxy-tetrahydrocannabinol, 5'-azido-$\Delta^8$-tetrahydrocannabinol, AMG-1, AMG-3, AM411, AM708, AM836, AM855, AM919, AM926, AM938, cannabidiol propyl analogue (CBDV), cannabichromene propyl analogue, cannabigerol, CP 47497, CP 55940, CP 55244, CP 50556, CT-3 (ajulemic acid), dimethylheptyl HHC, HU-210, HU-211, HU-308, WIN 55212-2, desacetyl-L-nantradol, dexanabinol, JWH-051, levonantradol, L-759633, nabilone, 0-1184, and mixtures thereof. In addition, terpenes present in extracted *cannabis* oils provide additional desired qualities when effectively administered.

SEDDS systems have not been used with cannabinoids for multiple reasons; first, due to the possibility of drug or formulation stability resulting from the SEDDS processing; or that the emulsifying system may result in too rapid of absorption and higher peak concentrations of the drug; and lastly, large concentrations of surfactant in the SEDDS system may cause skin irritation. It is thus an embodiment of the present disclosure to develop a SEDDS for delivery of extracted *cannabis*, focusing on factors critical to achieving enhanced bioavailability, increased chemical and enzymatic stability, enhanced *cannabis* derivative dissolution, higher interfacial absorption area, and enhanced permeation. While difficulties in optimizing SEDDS formulations traditionally require specific attention to the active pharmaceutical ingredient (API) characteristics, the present disclosure requires development of a SEDDS comprising entire extracted *cannabis* oils or *cannabis* preparations comprising multiple derivatives of *cannabis*.

The present disclosure presents a novel aqueous self-emulsifying drug delivery system (SEDDS) *cannabis* preparation capable of transdermal administration through a fast acting gel or sustained-release transdermal patch. In one embodiment, preparations involving *cannabis* extracts are presented to produce an oil-in-water emulsion in which the hydrophilic-lipophilic balance (HLB) is optimized to produce a stable emulsion. A blend of surfactants can further increase the stability of emulsions and create SEDDS.

Solvents such as alcohols [ethanol, isopropanol, propylene glycol, dipropylene glycol, diethylene glycol monoethyl ether (Transcutol), and glycerin] were screened for their solubility and stability in the formulation. These alcohols are known transdermal permeability enhancers and previous work (Touitou et al. 2000; Lodzki et al. 2003) has displayed higher encapsulation efficiency and greater micelle flexibility; resulting in higher transdermal permeability of lipophilic drugs including CBD. Surfactants are chosen in order to maintain a Hydrophilic-Lipophilic Balance (HLB) of 1-8, which also produce micelles that encapsulate *cannabis* ingredients. The HLB of a surfactant is a measure of the degree to which it is hydrophilic or lipophilic, determined by calculating values for the different regions of the molecule. Using the methodology described by Griffin in 1949, surfactants may be described as follows:

$$HLB = 20 * M_h / M$$

where $M_h$ is the molecular mass of the hydrophilic portion of the molecule, and M is the molecular mass of the whole molecule, giving a result on a scale of 0 to 20. An HLB value of 0 corresponds to a completely lipophilic/hydrophobic molecule, and a value of 20 corresponds to a completely lipophobic/hydrophilic molecule. The HLB value can be used to predict the surfactant properties of a molecule:

| | |
|---|---|
| <10 | Lipid-soluble (water-insoluble) |
| >10 | Water-soluble (lipid-insoluble) |
| 1 to 3 | Anti-foaming agent |
| 3 to 8 | W/O (water in oil) emulsifier |
| 7 to 9 | Wetting and spreading agent |
| 13 to 16 | Detergent |
| 8 to 16 | O/W (oil in water) emulsifier |
| 16 to 18 | Solubilizer or hydrotrope |

Surfactants may include: sorbitan trioleate, polysorbate 80, polysorbate 20, isopropyl myristate, medium chain triglycerides, Labrasol, capric/caprylic glycerides, oleic acid, stearic acid, lecithin, and phosphatidylcholine. Other surfactants and oils include: polyethoxylated surfactants, PEG-modified surfactants, mineral oil, vegetable oils (sesame, corn, cottonseed, almond, pecan, peanut, sunflower, safflower, olive, and soybean), animal oils, castor and coconut oil. An exemplary oil-in-water emulsion will orientate the polar heads of the surfactants outward, producing uni- to multi-lamellar structures, to increase dermal lipid fluidity and can penetrate intercellularly through the skin by their small size (<200 nm). These properties apply to all biological lipid bilayer membranes including transdermal permeability and flux.

In another embodiment, a variety of polymers and thickening agents can be employed to further stabilize the emulsion and provide favorable drug release properties. Acrylate based polymers were screened for stability and drug release include Carbopol 980, Carbopol 5984, Ultrez 10, Pemulen TR-1, and Pemulen TR-2. These polymers are acidic in nature and need a base to neutralize the pH. Common bases include: sodium hydroxide, potassium hydroxide, triethanolamine, arginine, or other suitable base. Additionally, other thickening agents can be used including: hydroxyethyl cellulose, hydroxypropylmethyl cellulose, locust bean gum, xanthan gum, and saponin containing extracts (*Quillaja* spp., *Yucca* spp., *Glycyrrhiza* spp.).

In one embodiment, the present disclosure features a transdermal composition for the delivery of a cannabinoid composition, including a pharmaceutically acceptable carrier suitable for transdermal delivery of the cannabinoid composition. Transdermal delivery is capable using compositions which pass through the stratum corneum of a subject, and may further pass through the dermis, epidermis, hypodermis, and may further reach underlying tissues and organs. Formulations suitable for transdermal administration may be presented as ointments, gels, or discrete patches adapted to remain in intimate contact with the epidermis of the subject for an extended period of time. Formulations suitable for transdermal administration may also take the form of an optionally buffered aqueous solution of the active compound.

Figure 4A:
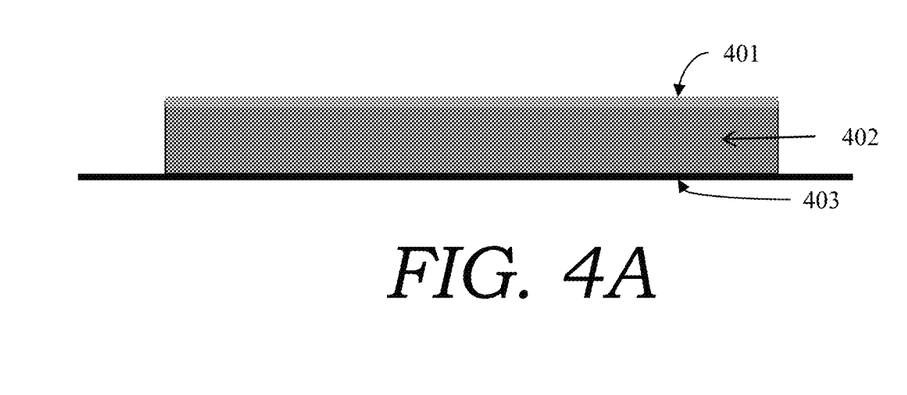
FIG. 4A depicts a monolithic transdermal patch used in Example 4.
Figure 4B:
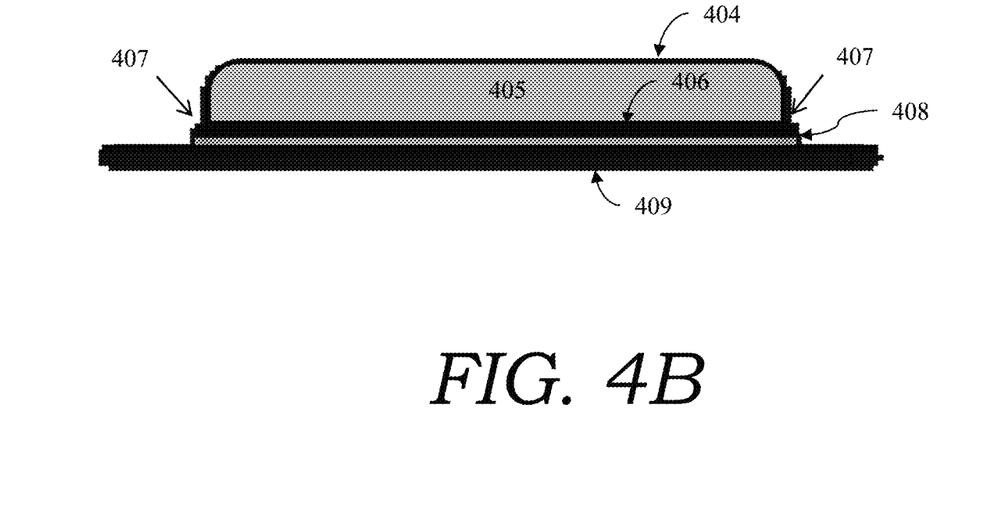
FIG. 4B depicts a reservoir transdermal patch used in Examples 5 and 6.

In one embodiment of the present disclosure, formulations for transdermal delivery can be utilized in a patch for sustained drug delivery. The subsequent patch can be monolithic, containing the backing film (polyester, polyethylene, polyethylene terephthalate, aluminum, polyolefin, and/or foam), the drug-containing matrix, and a release liner (film that resists adherence to the drug containing matrix, typically fluorocoated or siliconized polyester or polyethylene terephthalate). A multi-layered patch (FIG. 4B) can be created by encasing the transdermal preparation between a reservoir and a rate-controlling membrane for more sustained drug release. The reservoir is formed when the backing is heat sealed to the membrane and will contain the medicated gel. The membrane can be composed of ethylene vinyl acetate (EVA) wherein the vinyl acetate content is varied, commonly 4% to 19% (w/w), to accomplish the desired drug delivery rate. Other suitable membrane compositions include: silicone, polyurethane, polyethylene, polyvinyl, ethylene copolymers, polyamides, pyrrolidone, or cellulose-based materials. The gel within the reservoir will diffuse the drug through the membrane into the skin for controlled transdermal delivery.

Indeed the present disclosure provides for SEDDS comprising CBD, THC, and, related *cannabis* preparations comprising higher efficiencies than with typical hydrophobic API, resulting in mixtures capable of higher bioavailability, as is further described in the below examples.

EXAMPLES

The below examples set forth non-limiting embodiments, and for each example SEDDS preparations may be varied for suitable administration means known by those skilled in the art.

Example 1—Particle Size Analysis of Micelles

A fully suspended mixture of CBD (0.01% w/w total), ethanol (0.01% w/w total), sorbitan trioleate (0.016% w/w total), and polysorbate 80 (0.0002% w/w total) was prepared in water (99.91% w/w total) with disodium ethylenediaminetetraacetic acid (0.05% w/w total) as a preservative.

The solution is ultrasonicated to reduce the micelle particle sizes within the formulation. The remaining emulsion (pH=7.1) is stable for several days at room temperature but can be shaken to form a stable emulsion if separated after prolonged storage. High sheer homogenization and ultrasonication are common methods to reduce oil droplet size and increase stability of micelle preparations. Furthermore, centrifugation can be used to separate the micelle encapsulated CBD from the oil phase pellet. The pellet containing non-encapsulated CBD can be resuspended in water, mixed, and sonicated to obtain further micelle encapsulated CBD. This step can be repeated and the aqueous fractions combined and concentrated by vacuum lyophilization. Alternatively, the emulsion can be filtered through various membranes and porosities to obtain only the encapsulated micelles or by other methods known by those skilled in the art to obtain pure, encapsulated cannabinoid micelles.

Figure 1:
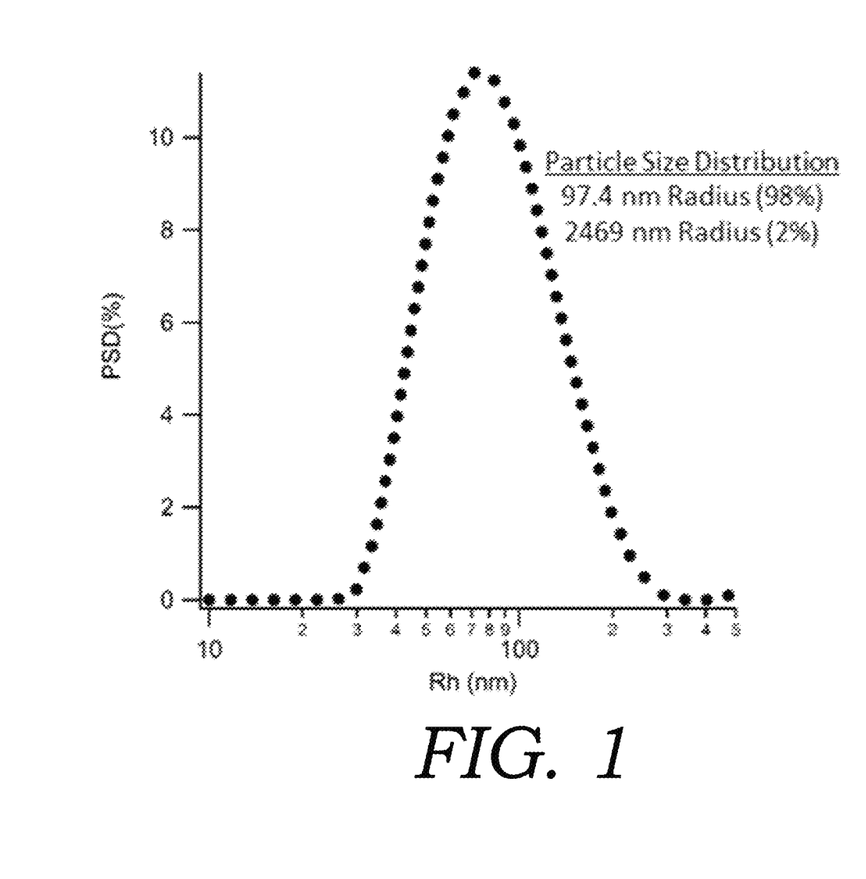
FIG. 1 depicts particle size distribution of micelles created in one emulsified formulation (Example 1).

Dynamic light scattering (DLS) is a technique to determine the hydrodynamic diameter of micelles using the Brownian and Stokes-Einstein equations. A Malvern Zetasizer was used to determine the size of formed micelle particles. Two distinct sizes were observed but the micelle diameter of 194.8 nm was strongly preferred, while only 2% of the micelles were a result of larger drug agglomerates (FIG. 1).

Example 2—CBD Transdermal Gel

The oil phase was prepared using pure CBD (10.0% w/w total) with ethanol (20.0% w/w total), oleic acid (9.9% w/w total) and polysorbate 20 (7.1% w/w total). Water is added slowly and the resulting microemulsion can undergo shear mixing, ultrasonication, or other methods referred to in Example 1 to increase encapsulation efficiency.

A secondary water phase is prepared by dispersing acrylate-based polymers, preferably Carbopol 980 (0.5% w/w total) in purified water and neutralized to pH=7 with suitable base. Glycerin (5.0% w/w total) is added as a humectant and mixed until a smooth, clear solution is obtained. A direct method wherein the microemulsion is added slowly into the water/polymer/glycerin matrix and mixed until a highly viscous ointment is obtained. Essential oils of *cannabis* and other botanicals are added at 1.2% (w/w total) and mixed to create a stable formulation. The essential oils are used as fragrance to increase the sensory application of the ointment and it is well known that terpenes can increase transdermal permeability (Smith 2015; Chen et al. 2016).

Figure 2:
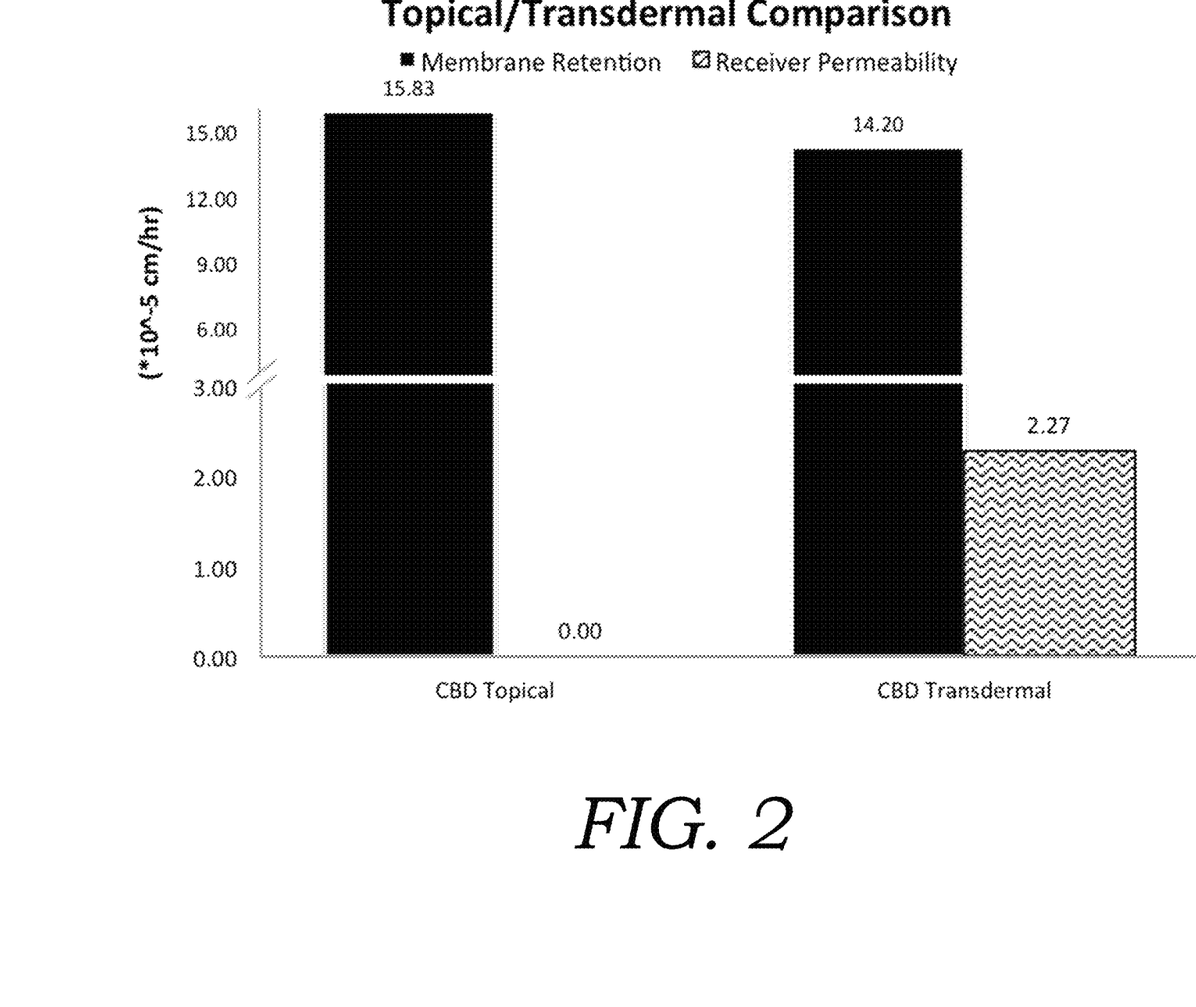
FIG. 2 depicts a permeability bar chart comparison of an encapsulated CBD transdermal vs. a non-encapsulated CBD preparation (Example 2).

A Franz Cell assay was used to determine the efficiency of the transdermal preparation in Example 2 when compared to a CBD topical prepared without encapsulation. Ingredients of the non-encapsulated CBD topical include: aloe barbadensis leaf juice, coconut and jojoba oil, peppermint oil, menthol, camphor, arnica, and eucalyptus. Strat-M (Millipore) membranes display linear correlations to human skin with high reproducibility and were used as a human skin substitute in permeability assays. The receiver solution, 10% ethanol, was incubated at 37° C. and sampled at regular intervals over 90 hours wherein CBD was quantified using high-performance liquid chromatography (HPLC). Upon completion of the experiment, the Strat-M membranes were removed, isopropyl alcohol was used to clean donor residue and allowed to dry prior to quantification to determine CBD retention in the membrane. Permeability is a relationship between the amount of drug delivered to the receiver as a function of donor drug concentration; a parameter used widely when comparing formulations. Similar CBD membrane retention was observed between both preparations, however the transdermal preparation was able to deliver CBD into the receiving well at a 2.18 µg/(cm$^2$*hr) rate. No CBD was detected in the receiving well with the non-encapsulated topical (FIG. 2).

Example 3—THC Transdermal Gel

The method of preparation was followed in Example 2 but using a THC-enriched extract (70.52% THC, 2.52% CBN 2.26% CBD, and 1.57% THCa) as the active ingredients.

Figure 3:
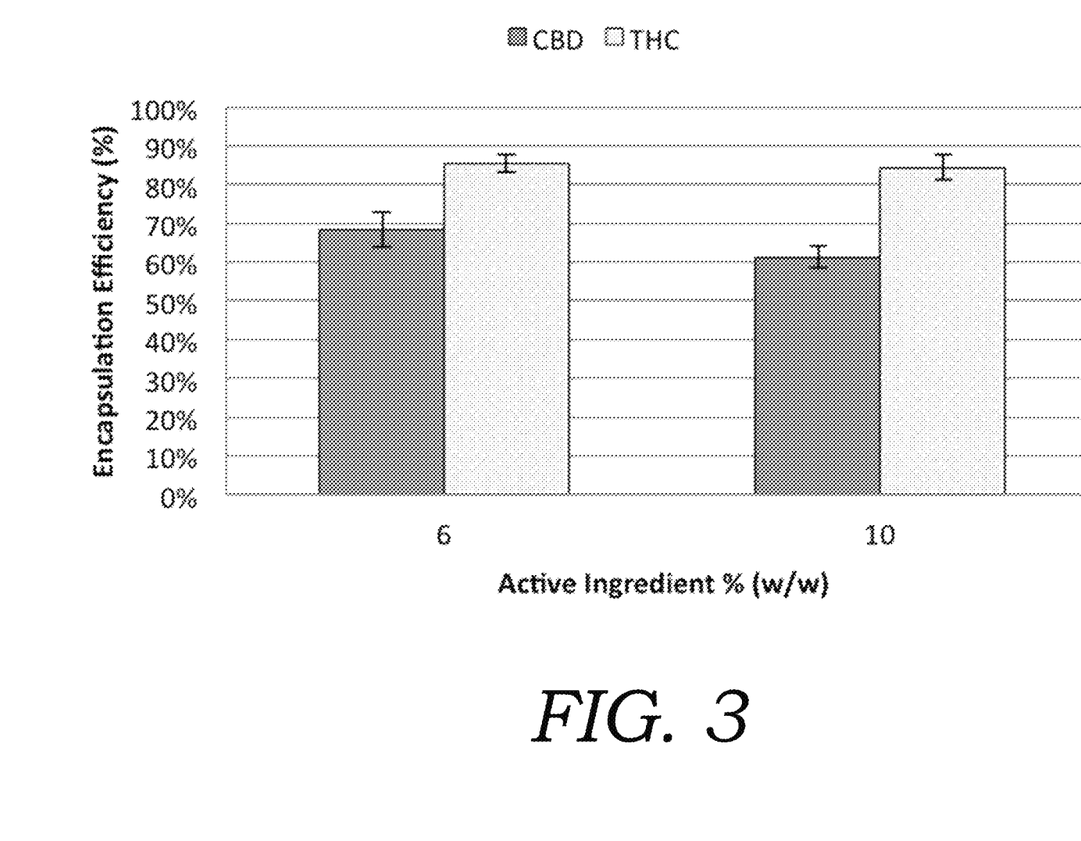
FIG. 3 depicts a bar chart showing encapsulation efficiencies of two different CBD (Example 2) and THC (Example 3) concentrations.

To determine the extent of cannabinoid encapsulation in CBD and THC preparations an ultracentrifugation method was adopted (Esposito et al. 2015; Touitou et al. 2000). Emulsions (n=3) were centrifuged using a high-speed microcentrifuge for 30 min at 15,000 rpm to separate the aqueous encapsulated micelles and the pelleted, non-encapsulated fraction. Acetonitrile was used to lyse micelles and solvate active ingredients. Encapsulation efficiency (% EE) was calculated by the amount of encapsulated cannabinoids as a proportion of the total cannabinoid concentration in formulation as determined by HPLC. Encapsulation efficiencies (FIG. 3) were compared between CBD and THC extracts. The encapsulation efficiency was generally higher for THC over CBD at the tested concentrations. The higher % EE for THC could be explained by low HLB, increased lipophilicity, and greater affinity for the hydrophobic tail of the encapsulation surfactants of oleic acid and polysorbate 20. An indirect relationship was observed between active ingredient concentration and encapsulation efficiency, but the result was not significant at 6% and 10% (w/w) THC and CBD. However, decreasing the active ingredient concentration to 1% (w/w) did increase encapsulation efficiency of CBD to 80.11%, a significant increase over 6% and 10% (w/w).

Example 4—CBD Monolithic Transdermal Patch

A monolithic transdermal patch system (FIG. 4A) comprises a backing 401, a drug-in-adhesive mix 402 and a release liner 403. The drug-in-adhesive mix 402 can be prepared using the oil-in-water emulsion described in Example 2 and mixing the oil-in-water emulsion with an acrylic (Duro-Tak 87-2516, Henkel) or polyisobutylene (Duro-Tak 87-6908, Henkel) and cast at 350 µm onto the fluorocoated side of a release liner (Scotchpak 1022, 3M). The resulting drug-containing matrix is dried to remove adhesive solvent, preferably to a dry thickness of 100-150 µm. The drug-coated release liner 403 is then pressure laminated to a polyester backing 401, such as CoTran 9718 or Scotchpak 9730 (3M); the resulting laminate can be die-cut or by other means known by those skilled in the art to create individual patches.

Example 5—CBD Reservoir Patch with Rate-Controlling Membrane

A reservoir patch system (FIG. 4B) comprises a backing 404, a drug reservoir 405, a rate-controlling membrane 406, a heat seal (backing to the membrane) 407, an adhesive layer 408, and a release liner 409. Adhesive is wet cast (100 µm) onto a release liner 409 described in Example 4 and dried to a thickness of 25 µm. The coated release liner 409 is then laminated onto a rate-controlling membrane 406 containing 9% ethylene vinyl acetate (EVA), preferably CoTran 9702 (3M). A backing film, or backing 404 described in Example 4, but containing EVA or another heat-sealable component, is then heat-sealed to the rate-controlling membrane 406 to contain the medicament, or drug, reservoir 405. The preferred occlusive backing films 404 are Scotchpak 1012 or CoTran 9722 (3M). The oil phase was prepared containing CBD (4.3% w/w total), Transcutol (10.0% w/w total), polysorbate 20 (5.0% w/w total), and ethanol (30.0% w/w total). Hydroxyethylcellulose (2.0% w/w total) is dispersed into the oil phase and purified water is added to create the encapsulated gel. The medicament is heat-sealed between the rate controlling membrane 406 and backing 404 at a concentration of 35 mg/cm$^2$ relative to final patch size. Die cutting can be used to cut out the patches to a standard size, most preferably 11.8 cm$^2$.

Example 6—THC Reservoir Patch with Rate-Controlling Membrane

The method of preparation was followed in Example 5 but using a THC-enriched extract (92.69% THC, 4.12% CBG, 1.07% CBC, and 0.83% CBD) as the active ingredients representing the cannabinoid preparation of the present invention.

Figure 5:
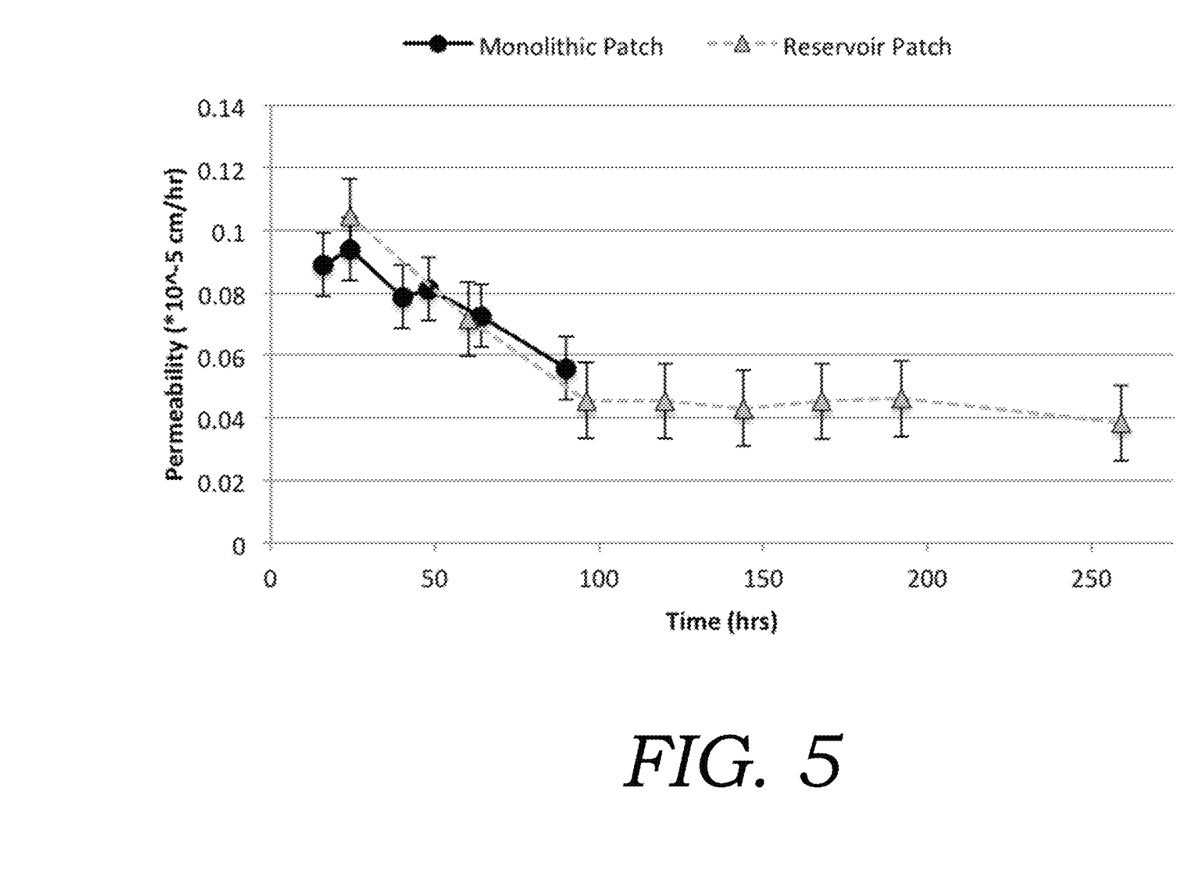
FIG. 5 depicts CBD dosing (permeability) with respect to time for a monolithic (Example 4) and reservoir (Example 5) patch.

The monolithic (Example 4) and reservoir patch (Example 5) were tested on Franz Cells using an identical method in Example 2. Linear, zero order delivery of CBD from the monolithic patch was observed over 60 hours but delivery rates dropped sharply after 90 hours. The reservoir patch was able to sustainably extend delivery through 260 hours (FIG. 5) with longer delivery rates attributed to the multi-layer design with rate-controlling membrane. Average CBD flux of 0.065 μg/(cm$^2$*hr) to receiver was determined for the reservoir patch. Patch reservoir gels were sampled for CBD concentration upon completion of in vitro and in vivo analysis with qualified patient volunteers who wore the patch on a flat, intact piece of skin. Delivery rates were increased 3.5× for in vivo patches and could be associated to several factors including lack of hair follicles or other active dermal receptors, including those connected to the endocannabinoid system (ECS), in synthetic membranes. Therefore, a corrected delivery of 2.7 μg/hr CBD is attainable over 72 hours; this assumption is further confirmed with 99% CBD release from the reservoir after 72 hours of in vivo patch dosing.

Figure 6:
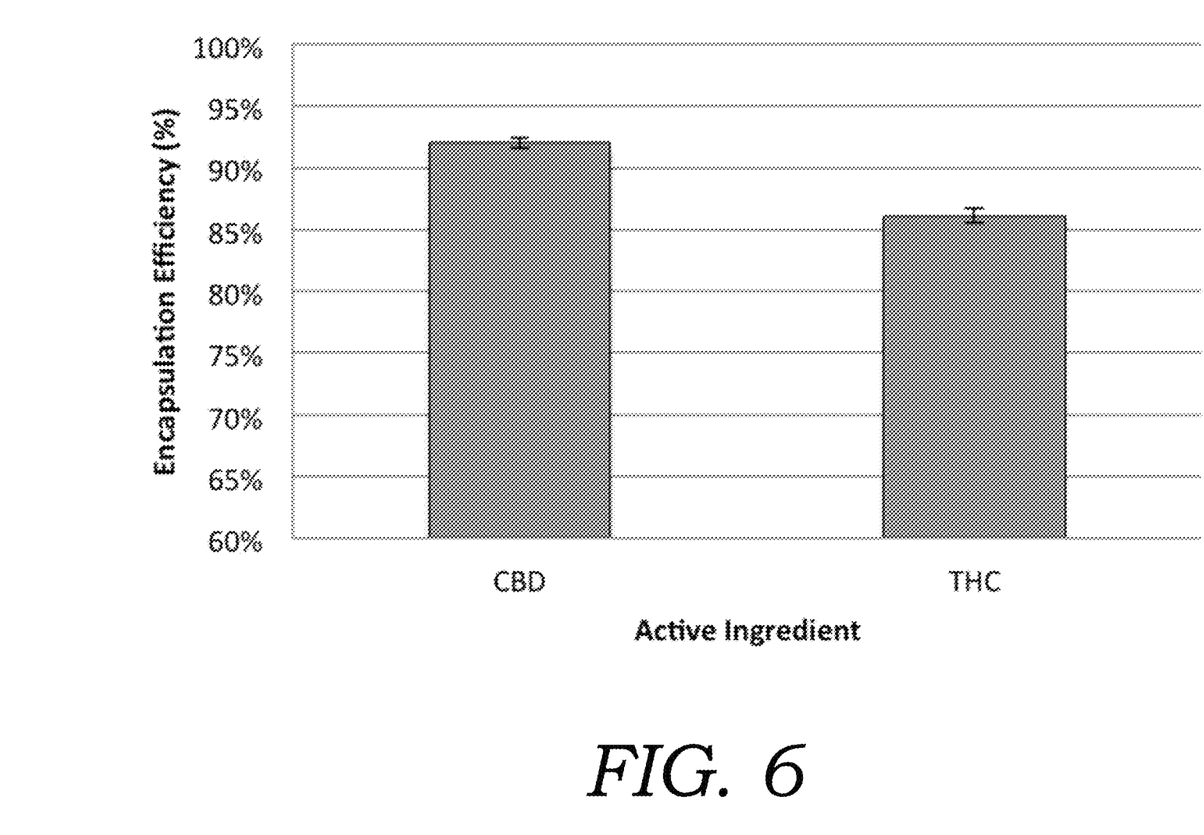
FIG. 6 depicts a bar chart showing encapsulation efficiencies of CBD and THC in Examples 5 and 6.

Preparations of CBD (Example 5) and THC (Example 6) were evaluated for encapsulation efficiency. Encapsulation of CBD and THC were determined to be 86.14% and 92.02%, respectively (FIG. 6). Encapsulation favored the more polar CBD using Transcutol and polysorbate 20, both co-solvent and surfactants are higher HLB than Examples 2 and 3; further showing the versatility of these SEDDS compositions.

Compositions of the present invention were analyzed for efficacy on various symptoms or conditions by patients who use medical *cannabis* to treat their condition. In the patients surveyed, the average age was 50 while the median age was 59; 57% of respondents were male while the remaining 43% were female. Five out of seven patients (71%) noted the transdermal patches were effective for pain relief. Three out of three respondents (100%) noted effective relief for anxiety after using the transdermal patch compositions of the present invention. Subject responses are set forth in Table 1 below.

TABLE 1

Subject survey responses.

|  | Pain | Anxiety |
|---|---|---|
| Total Patient Responses | 7 | 3 |
| Effective Relief | 5 | 3 |
| Neutral Relief | 2 | 0 |
| Non Effective Relief | 0 | 0 |

It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

REFERENCES

1. Griffin, William C. (1949), "Classification of Surface-Active Agents by 'HLB'", Journal of the Society of Cosmetic Chemists, 1 (5): 311-26
2. Chen J, Jian Q D, Chai Y P, Zhang H, Penn P, Yang X X. Natural terpenes as penetration enhancers for transdermal drug delivery. *Molecules.* 2016, 21, 1709.
3. Esposito E, Fantin L, Drechsler M, Mariani P, Contado C, Ruokolainen J, Ratano P, Campolngo P, Trezza V, Nastruzzi C, Cortesi R. Cannabinoid antagonist in nanostructured lipid carriers (NLC): design, characterization, and in vivo study. *Mater. Sci Eng.* 2015, 48, 328-336.
4. Hung O, Zamecnik J, Shek P N, Tikuisis P. Pulmonary delivery of liposome-encapsulated cannabinoids. International Patent No. 01/0366.
5. Keller B C, Fisher D L, Kiss S. Delivery of biologically active material in a liposomal formulation for administration into the mouth. U.S. Pat. No. 5,891,465.
6. Kwon, G S. Micelle encapsulation of therapeutic agents. U.S. patent application Ser. No. 12/668,269.
7. Lodzki M, Godin B, Rakou L, Mechoulam R, Gallily R, Touitou E. Cannabidiol-transdermal delivery and anti-inflammatory effect in a murine model. *J. Control. Release.* 2003, 93, 377-387.
8. Narang A S, Delmarre D, Gao D. Stable drug encapsulation in micelles and microemulsions. *Int. J. Pharm.* 2007, 345, 9-25.
9. O'Driscoll C M, Griffin B T. Biopharmaceutical challenges associated with with drugs with low aquous solubility—the potential impact of lipid-based formulations. *Adv. Drug Deliv. Rev.* 2008, 60, 617-624.
10. Smith N. Transdermal cannabinoid patch. US patent 2015/026316 filed Apr. 17, 2015.
11. Touitou E, Dayan N, Bergelson L, Godin B, Eliaz M. Ethosomes—novel vesicular carriers for enhanced delivery: characterization and skin penetration properties. *J. Control. Release.* 2000, 65, 403-418

What is claimed is:

1. A cannabinoid composition capable of trans canal delivery, comprising:
    a cannabinoid composition further comprising:
        a cannabinoid preparation ranging from 0.1% to 20% (w/w);
        at least one surfactant ranging from 5% to 50% (w/w);
        at least one co-solvent ranging from 10% to 70% (w/w);
        water ranging from 16% to 60% (w/w); and
    wherein the cannabinoid composition is capable of topical application and wherein the cannabinoid preparation is encapsulated by surfactants to form micelles having uni-, bi-, or multi-lamellar structures.

2. The cannabinoid composition of claim 1, wherein the at least one surfactant comprises two surfactants.

3. The cannabinoid composition of claim 2, wherein the two surfactants comprise air HLB in the range of 1 to 8 and form a self-assembling emulsion.

4. The cannabinoid composition of claim 1, wherein the at least one surfactant comprises an HLB in the range of 9-20.

5. The cannabinoid composition of claim 1, wherein the at least one surfactant is selected from a group consisting of: oleic acid, lecithin, phosphatidylcholine, isopropyl myristate, stearic acid, medium and long chain triglycerides (including Labrasol), polysorbate 20, polysorbate 80, or other ethoxylated surfactant, and sorbitan trioleate, or other sorbitan surfactant.

6. The cannabinoid composition of claim 1, wherein the at least one co-solvent is selected from a group consisting of methanol, ethanol, isopropyl alcohol, butanol, pentanol, hexanol, ethylene glycol, propylene glycol, dipropylene glycol, glycerol, erythritol, mannitol, sorbitol, diethylene glycol monoethyl ether (Transcutol), any derivative thereof, and combinations relating thereto.

7. The cannabinoid composition of claim 1, further comprising a thickening agent in the range of 0.01% to 5% (w/w).

8. The cannabinoid composition of claim 1, further comprising terpenes in the range of 0.1% to 5% (w/w).

9. The cannabinoid composition of claim 1, further comprising a preservative ranging from 0.01% to 2.5% (w/w).

10. The cannabinoid composition of claim 1, further comprising a pH modifying agent to neutralize the composition.

11. The cannabinoid composition of claim 1, wherein the cannabinoid composition is incorporated into a patch comprised of a reservoir and a backing film having an adhesive;
    wherein the patch reservoir is capable of operably containing the cannabinoid composition within the backing film, and is capable of operably affixing to skin via the adhesive for transdermal delivery of the cannabinoid composition.

12. The cannabinoid composition of claim 11, further comprising a rate-controlling membrane.

13. The cannabinoid composition of claim 11, further comprising a drug encased reservoir.

14. The cannabinoid composition of claim 1, wherein the cannabinoid composition for topical application in the form of an ointment, a cream, an emulsion, a lotion, a paste, an unguent, a gel or a sunscreen comprising therapeutically effective amounts of the cannabinoid composition.

* * * * *